United States Patent [19]

Bender

[11] Patent Number: 5,016,621

[45] Date of Patent: May 21, 1991

[54] KNEE BRACE

[75] Inventor: Kelly M. Bender, Ashland, Wis.

[73] Assignee: Mikros U.S.A., Inc., Ashland, Wis.

[21] Appl. No.: 484,897

[22] Filed: Feb. 26, 1990

[51] Int. Cl.$^5$ .............................................. A61F 3/00
[52] U.S. Cl. ................................ 128/80 C; 128/80 R; 128/85; 2/22; 2/24
[58] Field of Search .............. 128/80 R, 80 C, 88, 128/85, 77, 84 R; 2/22, 24

[56] References Cited

U.S. PATENT DOCUMENTS

| | | |
|---|---|---|
| 1,622,211 | 3/1927 | Sheehan ................................... 2/22 |
| 3,046,981 | 7/1962 | Biggs, Jr. et al. |
| 3,463,147 | 8/1969 | Stubbs . |
| 3,786,804 | 1/1974 | Lewis . |
| 3,817,244 | 6/1974 | Taylor . |
| 3,934,583 | 1/1976 | Hollingshead et al. ...... 128/80 C X |
| 3,945,046 | 3/1976 | Stromgren . |
| 4,064,874 | 12/1977 | Valin . |
| 4,116,236 | 9/1978 | Albert . |
| 4,296,744 | 10/1981 | Palumbo . |
| 4,366,813 | 1/1983 | Nelson . |
| 4,379,463 | 4/1983 | Meier et al. |
| 4,425,912 | 1/1984 | Harper .................................. 2/24 X |
| 4,492,227 | 1/1985 | Senn et al. ......................... 128/80 C |
| 4,791,916 | 12/1988 | Paez .................................... 128/80 C |
| 4,805,606 | 2/1989 | McDavid, III ................... 128/80 C |

FOREIGN PATENT DOCUMENTS 2553996  5/1985  France ............................. 128/80 C Primary Examiner—Richard J. Apley
Assistant Examiner—Jennifer L. Doyle
Attorney, Agent, or Firm—Burd, Bartz & Gutenkauf

[57] ABSTRACT

A knee brace including a tubular sleeve to encompass the knee region. An upper strap assembly includes first and second support straps that are fixed above the knee to sides of the sleeve. The free ends are fixed together and are extendable to a location beneath the knee to straddle the kneecap intension. A cymmetrical lower strap assembly has a pair of support straps fixed at one end to opposite sides of the sleeve at a location below the knee. The free ends are fixed together and are extendable to a location above the knee to also straddle the kneecap intension and tend to hold it in place during rigorous activity. Cross straps extend laterally from the point of fixation of the support straps.

18 Claims, 3 Drawing Sheets

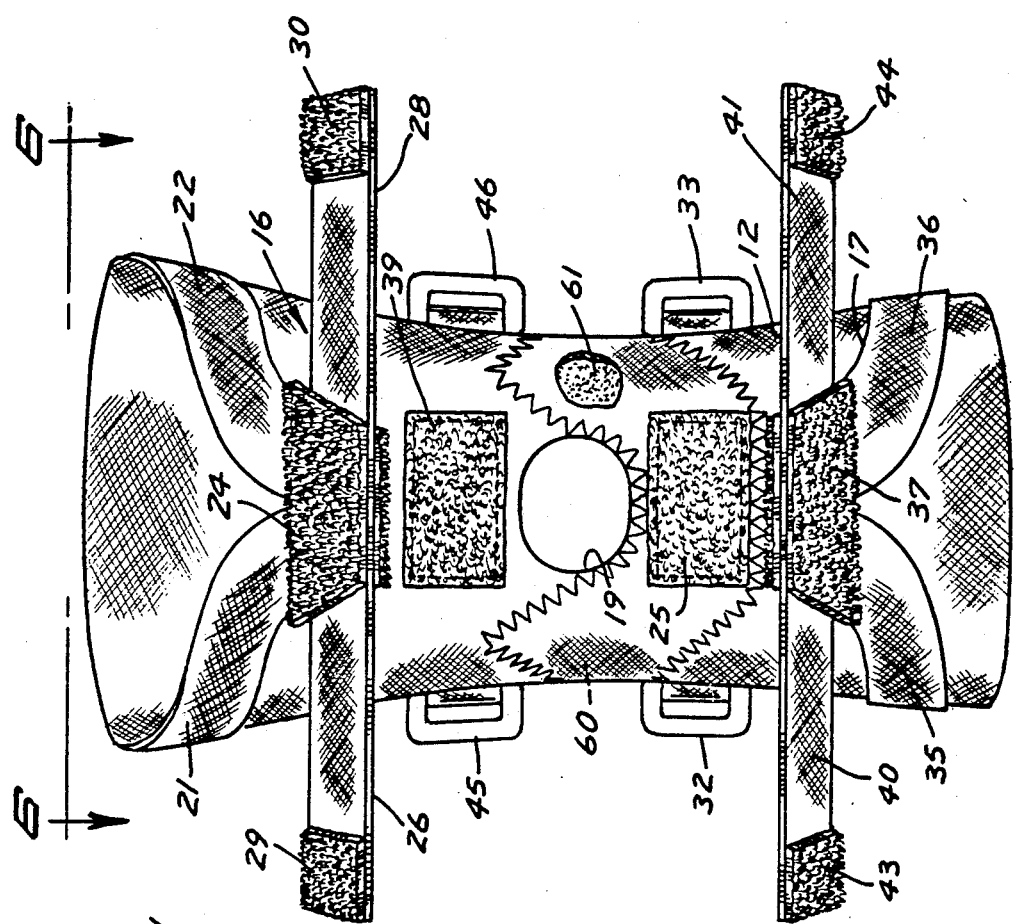
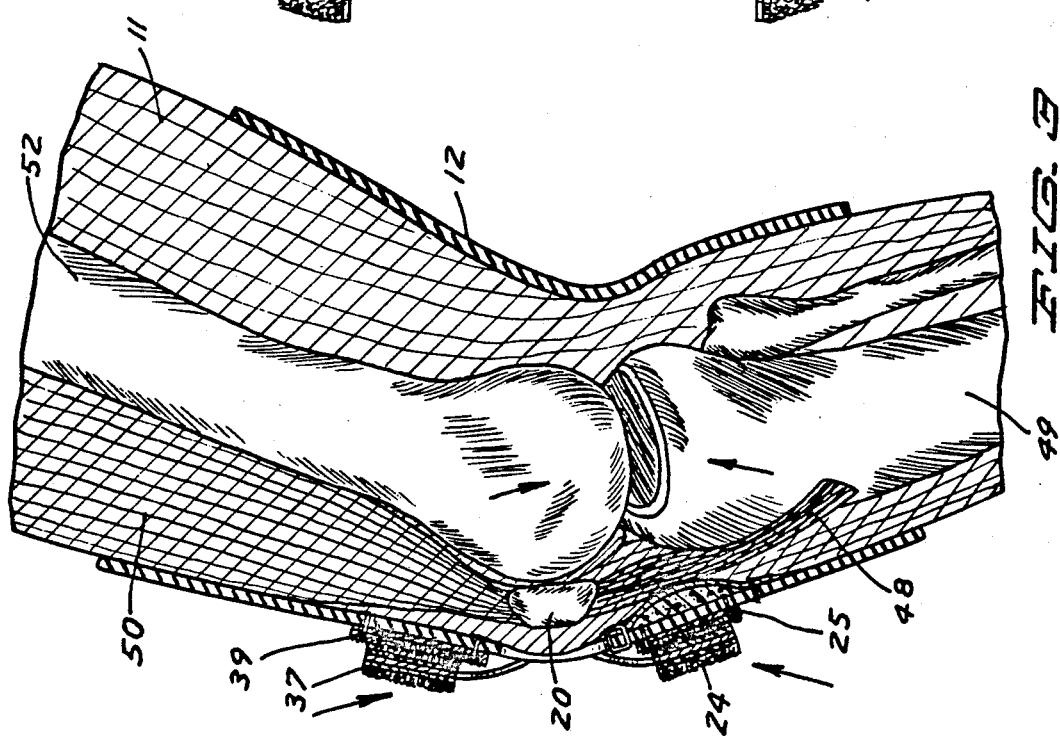

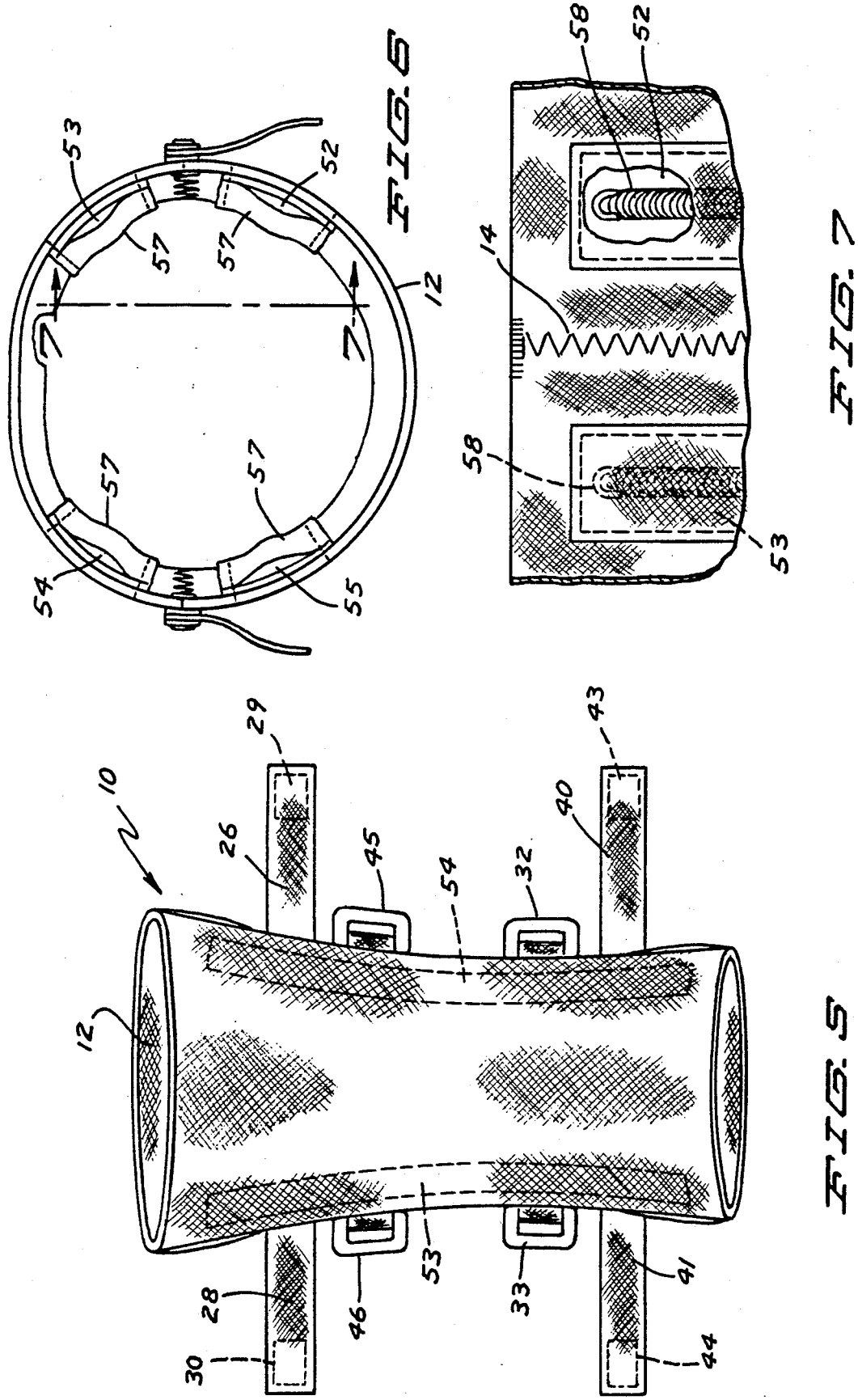

KNEE BRACE

BACKGROUND OF THE INVENTION

The knee joint is a compromise between mobility and stability. It is one of the most mobile joints in the body, at the expense of stability. Almost all injuries to the knee will restrict mobility. A frequent injury is associated with the patella tendon. The quadricep muscles connect to the quad tendon which attaches to the kneecap from above. The kneecap is attached to the tibia below by the patella tendon. When the knee bends the patella tendon stretches. When the bending is traumatic, the patella tendon tends to lift off of the tibia, sometimes taking some of the bone with it. This is particularly true of young athletes where the tendon has not yet totally osciffied. Another injury involves subluxation which is a misalignment of the joint occurring when the patella or kneecap moves laterally. Subluxation can also result in patella chondromalacia, having to do with the interface between the inner surface of the patella and the confronting ligaments and tendons.

SUMMARY OF THE INVENTION

The invention relates to a flexible knee brace for use by athletes and others engaged in rigorous activity, to support and stabilize the knee in order to protect it from injury or from aggravation of preexistent injury. The brace offers generalized support to the vicinity of the knee Joint and specifically supports the patella or kneecap to inhibit it from lateral movement and support it with respect to the quadricep tendon and the patella tendon. The brace includes an elastic base that covers the knee region from the lower thigh to the upper calf. Upper and lower strap assemblies are fixed to the base. The upper and lower strap assemblies are symmetrical. The upper strap assembly includes first and second elastic straps symmetrically fastened at one end to lateral sides of the base. The opposite ends come together and are adjacently fixed at an apex to form a V-configuration. The apex of the V-configuration is stretched to a location beneath the knee cap and fixed there by suitable means. The bottom strap assembly likewise has first and second elastic straps that are fixed to opposite lateral sides of the base and in a location substantially beneath the knee. The opposite ends come together at an apex to form a V-configuration. The support straps are stretched so that the apex is positioned at a location above the knee and fastened thereby suitable means. Transverse straps are provided at the apex of the V-configurations for further support. The V-configuration straps cross over above and below the knee and tend to hold the patella in place.

IN THE DRAWINGS

FIG. 3 is a view in section of the knee brace of FIG. 2 for purposes of illustrating the relationship of the knee brace to the parts of the leg;

FIG. 4 is a front elevational view of the knee brace of FIG. 1 removed from a leg and with the strap assemblies undone;

FIG. 5 is a rear elevational view of the knee brace of FIG. 4;

FIG. 6 is a top plan view of the knee brace of FIG. 4 taken along the line 6—6 thereof;

FIG. 7 is an enlarged view of a portion of the knee brace of FIG. 6 taken along the line 7—7 thereof with portions removed for purposes of illustration.

DESCRIPTION OF A PREFERRED EMBODIMENT

Figure 1:
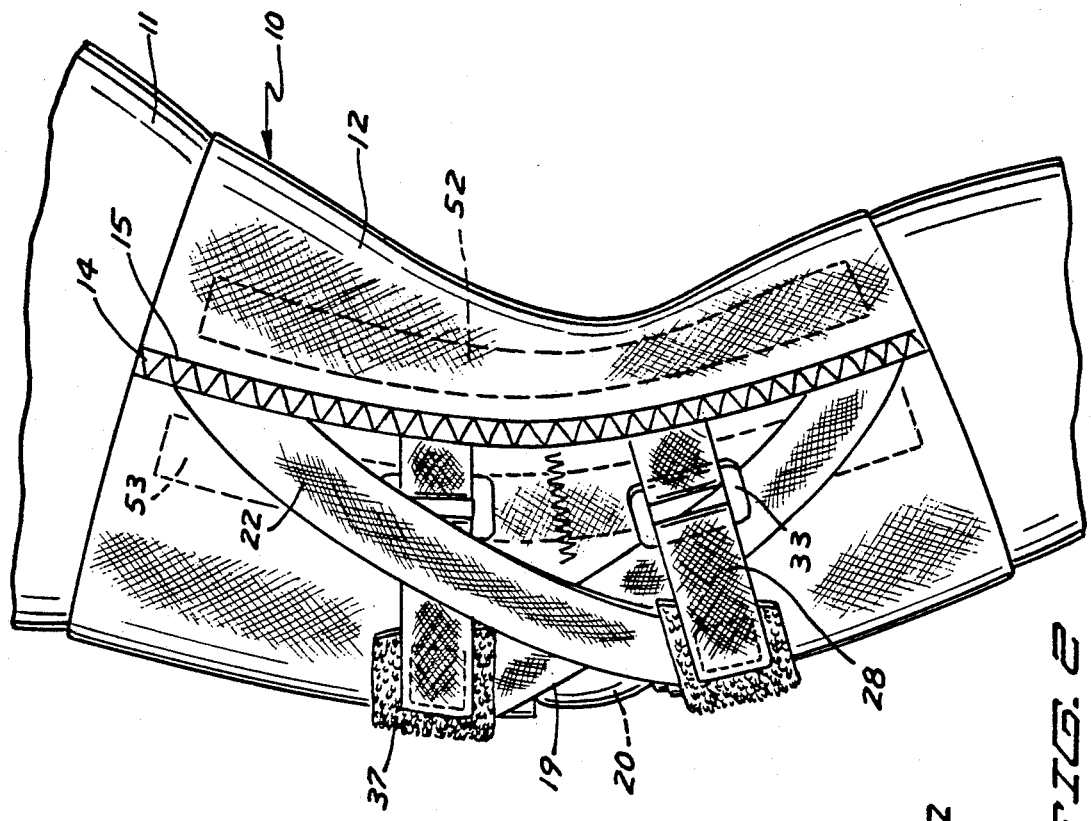
FIG. 1 is a front elevational view of a knee brace according to the invention installed upon a leg.
Figure 2:
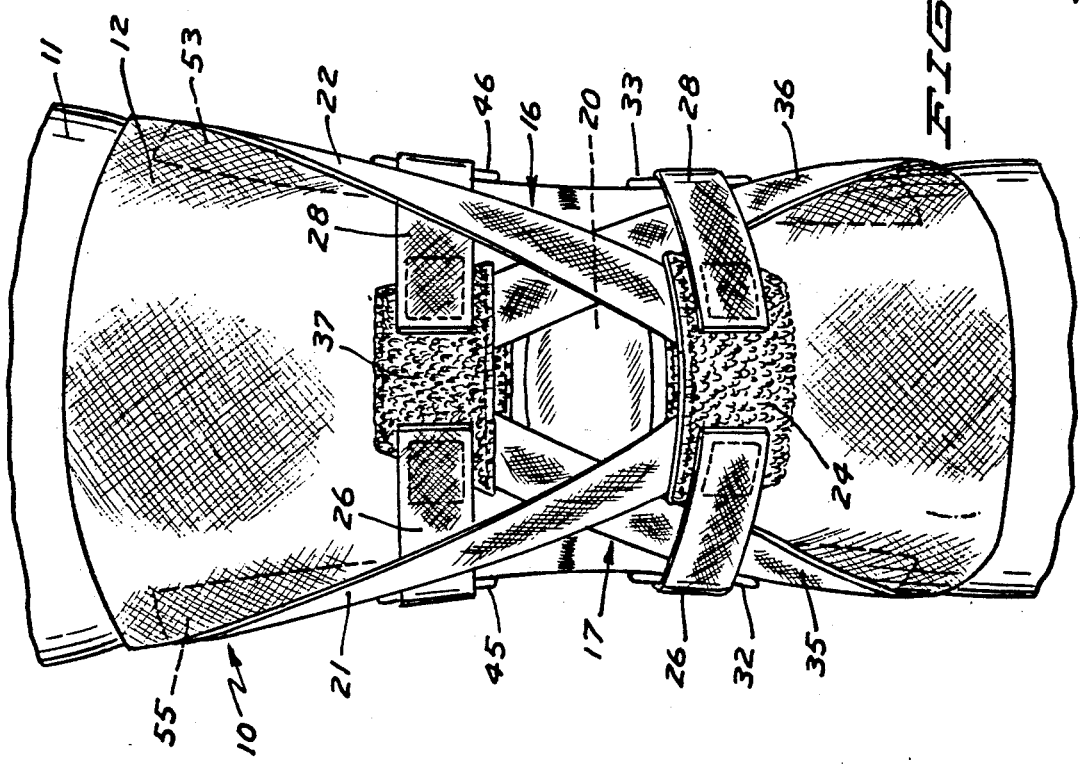
FIG. 2 is a side elevational view of the knee brace of FIG. 1.

Referring to the drawings, there is shown in FIGS. 1 and 2 a knee brace according to the invention indicated generally at 10 installed on a leg 11. Brace 10 includes a tubular sleeve or base 12 that covers the knee region from the lower thigh to the upper calf. Base 12 is contoured to closely fit the contour of leg 11 and is formed of an elastic material such as a neopreme type sheet material having a smooth surface on the side of the base facing the leg, and a textured surface facing out. Base 12 can be formed of front and back halves brought together in edge to edge relationship along lateral sides and sewn together in a butt seam with a zig zag stitch 14 and a reinforcing strip 15 on the outer side so as to present an uninterrupted surface facing the leg. Base 12 offers generalized support to the knee region.

Knee brace 10 includes upper and lower strap assemblies 16, 17 fixed to the base 12 and positioned to straddle the kneecap 20 at a kneecap site on the base to hold the kneecap in place. Upper and lower strap assemblies 16, 17 are symmetrical. Upper strap assembly 16 includes first and second equal length elastic support straps 21, 22. A first end of each of the support straps 21, 22 is fixed to a lateral side of the base 12 near the upper edge thereof. As shown in FIG. 2 the first or fixed end of second support strap 22 is fixed to the zig zag stitch 14 on a lateral side of the base 12 vertically spaced above the kneecap site. The first support strap 21 is similarly fastened on the opposite side. The support straps 21, 22 are longitudinally elastic. The second ends of the support straps 21, 22 opposite the fixed ends come toward one another to a point of adjacent relationship or to an apex forming a V-configuration. The second ends of support straps 21, 22 are fastened in adjacent relationship at the apex of the V-strap configuration by a first connecting member 24. As shown in FIG. 4, a first fastening pad 25 is fixed to the base 12 beneath a knee opening 19 and positioned to be located just beneath the kneecap 20. Fastening pad 25 has an outside surface of adhering material of the synthetic type that adheres when pressed together sold under the trademark Velcro. The connecting member 24 has an inside surface of adhering material. In assembled relationship, the support straps 21, 22 are stretched by pulling the connecting member 24 downwardly beyond the knee opening 19 and attaching it to the fastening pad 25. The support straps 21, 22 are in stretched relationship straddling the kneecap as shown in FIGS. 1 and 2.

A pair of cross straps 26, 28 extend laterally outwardly from the connecting member 24. Straps 26, 28 could be comprised as a single elongate strap connected at the connecting member 24. The outer ends of the cross straps 26, 28 have fastening strips 29, 30 of adhering material. A pair of D-loops 32, 33 are fastened to lateral sides of base 12 on opposite sides thereof circumferentially aligned with the first fastening pad 25. The D-loops 32, 33 are fastened to the base 12 by suitable means such as fabric loops stitched to the base closely adjacent the lateral seam 14. When the first connecting member 24 is engaged with the first fastening pad 25, the cross straps 26, 28 are trained through the D-loops 32, 33 and return to the fastening member 24. The outwardly facing surface of connecting member 24 also has adhering material. The fastening strips 29, 30 of the cross straps 26, 28 are brought back around the base 12 and are attached to the outwardly facing surface of the connecting member 24. In this configuration, the support straps 21, 22 are secured with respect to the kneecap 20. The connecting member 24 and cross straps 26, 28 are firmly pressed inwardly of the knee.

Lower strap assembly 17 is constructed like upper strap assembly 16, having first and second elastic support straps 35, 36, each fixed at a first end to opposite lateral sides of base 12 and preferably at the zig zag seam 14 on either side of base 12. Support straps 35, 36 are fixed to base 12 at a location well below the kneecap and in the vicinity of the upper calf near the lower edge of base 12. Second ends of support straps 35, 36 opposite the fixed ends come together at an apex forming a V-strap configuration and are fixed in adjacent relationship by a second connecting member 37. Connecting member 37 has an inwardly facing adhering surface. A second fastening pad 39 is located on sleeve 12 just above the kneecap site or knee opening 19 so as to be positioned immediately above the kneecap 20 when the brace 10 is properly installed on the leg 11. With brace 10 installed on a leg, second connecting member 37 is moved to a position of attachment with the second fastening pad 39. Support straps 35, 36 of the lower straps assembly are stretched in tension from lateral sides of base 12 in straddling relationship to the kneecap 20 to a position above it.

Lower strap assembly 17 has first and second cross straps 40, 41 that extend laterally from the second connecting member 37. The outer ends of cross straps 40, 41 have fastening strips 43, 44 FIG. 4) formed of adhering material. The outer surface of the second fastening member 37 also has a layer of adhering material. Third and fourth D-loops are located on lateral sides of the base 12 above the knee opening 19 and circumferentially aligned with the second fastening pad 39. Third and fourth D-loops 45, 46 are for connection with the first and second cross straps 40, 41 of the lower strap assembly 17. When the second connecting member 37 is attached to the second fastening pad 39, the first and second cross straps 40, 41 are trained through the third and fourth D-loops 45, 46. The end portions are brought forward around base 12 and attached to the outer facing adhering surface of the second connecting member 37.

With the upper and lower strap assemblies 16, 17 assembled in proper relationship installed on a leg 11, the brace 10 provides support to the knee vicinity as shown in FIG. 3. Upper support straps 21, 22 and lower support straps 35, 36 are in tension and straddle the kneecap to inhibit lateral movement. Lateral straps 29, 30 of the upper strap assembly 16 push inward on the patella tendon 48 and in particular support it in close relationship to the tibia 49. Lateral cross straps 43, 44 of the lower strap assembly 17 bear against the quadricep muscle 50 and urge it in close relationship to the femur 52. The upper and lower strap assemblies 16, 17 urge the tibia and femur together with a resultant compressive force on the knee joint. When the knee is flexed as in FIG. 2, the upper and lower support straps are stretched further and placed in additional tension to further hold the kneecap and the knee joint in place.

Base 12 has a plurality of longitudinal stay members located on the lateral sides thereof to further support the knee from undue rotation and to prevent bunching of the base 12. Longitudinal pockets 52, 53, 54, 55 are located on base 12. A pair of pockets straddle each lateral seam 14 of base 12, one pocket being forward of the lateral seam on either side, and one pocket being located rearward thereof. Each pocket is formed by the installation of an elongate strip of material 57 (FIG. 6) sewn on the interior surface of the base 12 parallel to the length thereof. A stay member 58 is located in each pocket. As shown in FIG. 7, each stay member 58 is of the variety comprised as a pair of interleaved, flattened helical spring elements. The stay members extend substantially the entire length of the base 12.

An arcuate pocket 60 is located in partial surrounding relationship to the knee opening 19, being interrupted at the upper portion thereof. A knee pad 61 is located in the pocket 60 for purposes of cushioning that portion of the knee joint.

While there has been shown and described one preferred embodiment of the invention, it will be apparent that changes and deviations may be had from the embodiment shown without departing from the scope and spirit of the invention.

The embodiments of the invention in which an exclusive property or privilege is claimed are defined as follows:

1. A knee brace comprising:
  a tubular sleeve positionable in covering relationship to a knee and adjacent leg portions with a knee cap site on the front surface thereof;
  a V-configuration strap assembly including first and second elastic straps with first ends fixed to opposite lateral sides of the sleeve in vertically spaced relationship from the kneecap site, and second ends fixed in adjacent relationship at an apex by a connecting member having an inside surface of adhering material, and first fastening means releasably connectable with the apex of the strap assembly and located adjacent the kneecap site on the sleeve vertically opposite the side of attachment of the first ends of the support straps and comprised as a fastening pad having an outside surface of adhering material whereby the apex of the strap assembly is releasably connectable to the fastening means with the support straps stretched in tension in straddling relationship to the kneecap when the sleeve is installed upon a leg.

2. A knee brace comprising:
  a tubular sleeve positionable in covering relationship to a knee and adjacent leg portions with a kneecap site on the front surface thereof;
  a V-configuration strap assembly including first and second elastic straps with first ends fixed to opposite lateral sides of the sleeve in vertically spaced relationship from the kneecap site, and second ends fixed in adjacent relationship at an apex, and first fastening means releasably connectable with the apex of the strap assembly and located adjacent the kneecap site on the sleeve vertically opposite the side of attachment of the first ends of the support straps whereby the apex of the strap assembly is connectable to the fastening means with the support straps stretched in tension in straddling relationship to the kneecap when the sleeve is installed upon a leg; and
  first and second lateral cross straps extended from the apex of the strap assembly, and means on laterally opposite sides of the sleeve for connection of the first and second cross straps to the sleeve.

3. A knee brace comprising:
  a tubular sleeve positionable in covering relationship to a knee and adjacent leg portions with a kneecap site on the front surface thereof;
  an upper strap assembly having first and second elastic support straps formed in a V-configuration with first ends fixed to opposite lateral sides of the sleeve in vertically spaced relationship above the kneecap site, and second ends fixed in adjacent relationship at an apex, and first fastening means releasably connectable with the apex of the strap assembly and located adjacent and vertically beneath the kneecap site on the sleeve whereby the apex of the strap assembly is connectable to the first fastening means with the support straps stretched in tension in straddling relationship to the kneecap when the sleeve is installed upon a leg;
  a lower strap assembly having first and second elastic support straps formed in a V-configuration with the first ends fixed to opposite lateral sides of the sleeve in vertically spaced relationship beneath the kneecap site and second ends fixed in adjacent relationship to one another at an apex, second fastening means located adjacent and vertically above the kneecap site whereby the apex of the lower strap assembly can be fastened to the second fastening means with the first and second support straps of the lower strap assembly stretched in tension in straddling relationship to the kneecap.

4. The knee brace of claim 3 wherein: said sleeve is elastic.

5. The knee brace of claim 4 wherein: said upper strap assembly includes first and second cross straps extended laterally from the apex, first connecting means having portions on laterally opposite sides of the sleeve in generally circumferential alignment with the first fastening means for connection of the cross straps of the upper strap assembly to the sleeve;
  said lower strap assembly having first and second cross straps extended laterally from the apex of the lower strap assembly, second connecting means having portions on laterally opposite sides of the sleeve generally in circumferential alignment with the second fastening means for connection of the cross straps of the lower strap assembly to the sleeve 6. The knee brace of claim 5 wherein: said first connecting means and second connecting means include D-loops connected to lateral sides of the sleeve.

7. The knee brace of claim 6 wherein: said first strap assembly has a first connecting member at the apex having an outwardly facing adhering surface, said first and second ends of the cross straps of the upper strap assembly having ends with adhering surfaces whereby the ends of the first and second cross straps can be trained through the D-loops and returned for attachment to the first connecting member:
  said lower strap assembly having a second connecting member at the apex having an outwardly facing adhering surface, said first and second cross straps of the lower strap assembly having ends with adhering surfaces whereby the cross straps can be trained through the D-loops and returned for attachment to the second connecting member.

8. A knee brace comprising:
  a tubular sleeve configured to fit a leg with an upper sleeve edge located at the lower thigh region and a lower sleeve edge located at the upper calf region, and a front surface with a kneecap accommodating site;
  an upper strap assembly including a first elastic support strap having a first end connected to one side of the sleeve proximate the upper edge and a second movable end, a second elastic support strap having a first end connected to the opposite side of the sleeve proximate the upper edge and a second movable end, means connecting the movable ends of the first and second support straps of the upper support strap assembly, first means located adjacent and below the kneecap site for attaching the second ends of the first and second support straps of the upper strap assembly to the sleeve in adjacent relationship at a location beneath the kneecap site whereby the first and second support straps of the upper strap assembly straddle the kneecap in tension;
  a lower strap assembly including a first elastic support strap having a first end connected to one side of the sleeve proximate the lower edge and a second movable end, a second elastic support strap having a first end connected to the opposite side of the sleeve proximate the lower edge and a second movable end, means connecting the movable ends of the first and second support straps of the lower support strap assembly, second means located adjacent and above the kneecap site for attaching the second ends of the first and second support straps of the lower strap assembly to the sleeve in adjacent relationship at a location above the kneecap site whereby the first and second support straps of the lower strap assembly straddle the kneecap in tension.

9. The knee brace of claim 8 wherein: the second ends of the first and second support straps of the upper strap assembly are joined at a first apex, said first means for attaching the second ends of the first and second support straps to the sleeve including first fastening means located beneath the kneecap site releasably attachable to the first apex;
  the second ends of the first and second support straps of the lower strap assembly being joined at a second apex, said second means for attaching the second ends of the first and second support straps of the lower strap assembly to the sleeve including second fastening means located above the kneecap site releasably attachable to the second apex.

10. A knee brace comprising:
  a tubular sleeve configured to fit a leg with an upper sleeve edge located at the lower thigh region and a lower sleeve edge located at the upper calf region, and a front surface with a kneecap accommodating site;
  an upper strap assembly including a first elastic support strap having a first end connected to one side of the sleeve proximate the upper edge and a second movable end, a second elastic support strap having a first end connected to the opposite side of the sleeve proximate the upper edge and a second movable end, said second ends of the support straps joined at a first apex, first releasable fastening means located beneath the kneecap site for attaching the first apex to the sleeve at a location beneath the kneecap site whereby the first and second support straps of the upper strap assembly straddle the kneecap in tension;

a lower strap assembly including a first elastic support strap having a first end connected to one side of the sleeve proximate the lower edge and a second movable end, a second elastic support strap having a first end connected to the opposite side of the sleeve proximate the lower edge and a second movable end, said second ends of the support straps joined at a second apex, releasable fastening means located above the kneecap site for attaching the second apex to the sleeve at a location above the kneecap site whereby the first and second support straps of the lower strap assembly straddle the kneecap in tension;

said upper strap assembly having first and second cross straps extended laterally from the first apex, first connecting means having portions on laterally opposite sides of the sleeve in generally circumferential alignment with the first fastening means for connection of the cross straps of the upper strap assembly to the sleeve;

said lower strap assembly having first and second cross straps extended laterally from the second apex, second connecting means having portions on laterally opposite sides of the sleeve generally in circumferential alignment with the second fastening means for connection of the cross straps of the lower strap assembly to the sleeve.

11. The knee brace of claim 10 including: a plurality of longitudinal pockets located on the sleeve, and a corresponding plurality of resiliant stay members, one stay member being located in each pocket.

12. The knee brace of claim 11 wherein: each stay member is comprised of a pair of helical interleaved flattened spring elements.

13. The knee brace of claim 10 wherein: said first connecting means and second connecting means include D-loops connected to lateral sides of the sleeve.

14. The knee brace of claim 13 wherein: said first strap assembly has a first connecting member at the first apex having an outwardly facing adhering surface, said first and second ends of the cross straps of the upper strap assembly having ends with adhering surfaces whereby the ends of the first and second cross straps can be trained through the D-loops and returned for attachment to the first connecting member;

said lower strap assembly having a second connecting member at the second apex having an outwardly facing adhering surface, said first and second cross straps of the lower strap assembly having ends with adhering surfaces whereby the cross straps of the lower strap assembly can be trained through the D-loops and returned for attachment to the second connecting member.

15. The knee braces of claim 10 wherein: said first fastening means includes a first fastening pad with an outward surface of adhering material, said first apex having an inward surface of adhering material for attachment to the first fastening pad;

said second fastening means including a second fastening pad with an outward surface of adhering material, said second apex having an inward surface of adhering material for attachment to the second fastening means.

16. The knee brace of claim 15 wherein: said first apex includes a first connecting member connecting the second ends of the first and second support straps of the upper strap assembly, and said second apex including a second connecting member connecting the second ends of the support straps of the lower strap assembly.

17. The knee brace of claim 16 including: a plurality of longitudinal pockets located on the sleeve and a corresponding plurality of resilient stay member, one stay member being located in each pocket.

18. The knee brace of claim 17 wherein: each stay member is comprised of a pair of interleaved helical flattened spring elements.

* * * * *

UNITED STATES PATENT AND TRADEMARK OFFICE
CERTIFICATE OF CORRECTION

PATENT NO. : 5,016,621

DATED : May 21, 1991

INVENTOR(S) : Kelly M. Bender

Page 1 of 2

It is certified that error appears in the above-identified patent and that said Letters Patent is hereby corrected as shown below:

| Column | Line | |
|---|---|---|
| Abstract | 6 | "intension" should be -- in tension --. |
| Abstract | 6 | "symmetrical" should be -- symmetrical --. |
| Abstract | 11 | "intension" should be -- in tension --. |
| 1 | 18 | "osciffied" should be "ossciffied --. |
| 1 | 31 | "Joint" should be -- joint --. |
| 2 | 15 | "neopreme" should be -- neoprene --. |
| 3 | 21 | "Just" should be -- just --. |
| 3 | 35 | "Figure 4)" should be -- (Figure 4) --. |
| 3 | 36 | Following "material" insert -- . --. |
| 3 | 54 | Following "movement" insert -- . --. |
| 7 | 30 | "resiliant" should be -- resilient --. |
| 8 | 15 | "braces" should be -- brace --. |

UNITED STATES PATENT AND TRADEMARK OFFICE
CERTIFICATE OF CORRECTION

PATENT NO. : 5,016,621

DATED : May 21, 1991

INVENTOR(S) : Kelly M. Bender

It is certified that error appears in the above-identified patent and that said Letters Patent is hereby corrected as shown below:

Column 8, line 34 "member" should be -- members --.

Signed and Sealed this

Twenty-ninth Day of September, 1992

Attest:

DOUGLAS B. COMER

*Attesting Officer*     *Acting Commissioner of Patents and Trademarks*